United States Patent
Koons (10) Patent No.: US 6,582,445 B1
(45) Date of Patent: Jun. 24, 2003

(54) TREPHINE FOR LAMELLAR KERATECTOMY

(75) Inventor: Stephen J. Koons, Sunnyvale, CA (US)

(73) Assignee: Visx, Incorporated, Santa Clara, CA (US)

(*) Notice: Subject to any disclaimer, the term of this patent is extended or adjusted under 35 U.S.C. 154(b) by 0 days.

(21) Appl. No.: 09/265,025

(22) Filed: Mar. 8, 1999

Related U.S. Application Data (60) Provisional application No. 60/077,642, filed on Mar. 11, 1998.

(51) Int. Cl.$^7$ .................................................. A61F 9/00
(52) U.S. Cl. ....................................................... 606/166
(58) Field of Search ........................ 606/1, 4, 5, 166, 606/167, 161, 10, 13, 6; 30/300, 310, 435

(56) References Cited

U.S. PATENT DOCUMENTS

| | | | |
|---|---|---|---|
| 4,180,075 A | | 12/1979 | Marinoff |
| 4,205,682 A | * | 6/1980 | Crock et al. ................ 606/166 |
| 4,406,285 A | | 9/1983 | Villasenor et al. |
| 4,423,728 A | | 1/1984 | Lieberman |
| 4,429,696 A | | 2/1984 | Hanna |
| 4,619,259 A | * | 10/1986 | Graybill et al. ............ 606/166 |
| 4,662,370 A | | 5/1987 | Hoffmann et al. |
| 4,665,913 A | | 5/1987 | L'Esperance, Jr. |
| 4,669,466 A | | 6/1987 | L'Esperance |
| 4,732,148 A | | 3/1988 | L'Esperance, Jr. |
| 4,770,172 A | | 9/1988 | L'Esperance, Jr. |
| 4,773,414 A | | 9/1988 | L'Esperance, Jr. |
| 4,840,175 A | | 6/1989 | Peyman |
| 4,903,695 A | | 2/1990 | Warner et al. |
| 5,009,660 A | * | 4/1991 | Clapham .................... 606/166 |
| 5,133,726 A | | 7/1992 | Ruiz et al. |
| 5,163,934 A | | 11/1992 | Munnerlyn |

(List continued on next page.)

FOREIGN PATENT DOCUMENTS

| | | | |
|---|---|---|---|
| DE | DT197803 | * 3/1978 | ................ 606/166 |
| GB | 2242835 | * 10/1991 | |
| WO | WO 97/12272 | 4/1997 | |

OTHER PUBLICATIONS

Moreira et al., "Multifocal corneal topographic changes with excimer laser photorefractive keratectomy" *Arch. Ophthalmol.* (1992) 110:994–999.

Anschütz, "Laser correction of hyperopia and presbyopia" *International Ophthalmology Clinics*, Serdarevic, O.N., Editor, Little, Brown and Company, Publishers, Boston, (1994) 34(4):107–137.

Krueger et al., "New directions in excimer laser surgery" *Color Atlas/Text of Excimer Laser Surgery*, Thompson et al., Editors, Igaku–Shoin, Publishers, New York, Chapter 11, pp. 151.137.

Primary Examiner—Michael J. Milano
Assistant Examiner—(Jackie)Tan-Uyen T. Ho
(74) Attorney, Agent, or Firm—Townsend and Townsend and Crew LLP (57) ABSTRACT

A trephine can separate a cornea into at least two portions by applanating and cutting a boundary around an area of the cornea. The trephine comprises a flat ring for applanating the cornea and a blade for cutting the applanated cornea. The blade extends radially inward and is rotatable around the ring. Such a trephine can cut substantially parallel to the flattened lamella and causes lamellar separation at the cut depth. A flap of cornea may be separated from the remaining corneal tissue along the lamella by teasing the portions apart, or by injecting fluid between the lamellae. An exposed surface of the separated cornea may then be ablated with a laser and the flap reattached to the remaining corneal tissue.

33 Claims, 6 Drawing Sheets

U.S. PATENT DOCUMENTS

| | | | |
|---|---|---|---|
| 5,171,254 A | * 12/1992 | Sher | 606/166 |
| 5,215,104 A | 6/1993 | Steinert | |
| 5,290,301 A | 3/1994 | Lieberman | |
| 5,314,422 A | 5/1994 | Nizzola | |
| 5,395,356 A | 3/1995 | King et al. | |
| 5,430,946 A | * 7/1995 | Peters et al. | 30/310 |
| 5,441,511 A | * 8/1995 | Hanna | 606/166 |
| 5,486,188 A | * 1/1996 | Smith | 606/166 |
| 5,507,759 A | * 4/1996 | Nordan | 606/166 |
| 5,533,997 A | 7/1996 | Ruiz | |
| 5,556,395 A | 9/1996 | Shimmick et al. | |
| 5,556,406 A | * 9/1996 | Gordon et al. | 606/22 |
| 5,586,980 A | 12/1996 | Kremer et al. | |
| 5,624,456 A | 4/1997 | Hellenkamp | |
| 5,643,299 A | 7/1997 | Bair | |
| 5,653,723 A | 8/1997 | Kamerling et al. | |
| 5,685,998 A | 11/1997 | Shannon et al. | |
| 5,690,657 A | 11/1997 | Koepnick | |
| 5,715,032 A | 2/1998 | Isenberg | |
| 5,876,415 A | * 3/1999 | Pierce et al. | 606/166 |
| 5,944,731 A | * 8/1999 | Hanna | 606/166 |
| 5,951,579 A | * 9/1999 | Dykes | 606/167 |
| 6,052,909 A | * 4/2000 | Gardner | 30/300 |
| 6,350,272 B1 | * 2/2002 | Kawesch | 606/166 |

* cited by examiner

TREPHINE FOR LAMELLAR KERATECTOMY

CROSS-REFERENCE TO RELATED APPLICATIONS

This application claims the benefit of priority from U.S. Provisional Patent Application Ser. No. 60/077,642, filed Mar. 11, 1998, the full disclosure of which is incorporated herein by reference.

BACKGROUND OF THE INVENTION

The present invention relates generally to refractive surgery, and in particular, provides a trephine and method which are well particularly well suited for separating a portion of a cornea along a lamella. Refractive surgery of a human eye may be used to treat myopia, hyperopia, astigmatism and certain corneal anomalies. Refractive surgery generally involves reshaping layers of the cornea to improve the refraction of light rays passing through the cornea. Refractive surgical methods include radial keratotomy, photorefractive keratectomy, and others.

The cornea, the transparent dome-shaped anterior portion of the eye, includes several distinct tissue layers. The anterior surface of the cornea is coated by a tear film, which covers the corneal epithelium. The protective epithelial tissue layer includes several layers of cells covering the front of the cornea. Below the epithelial layer is Bowman's layer. Bowman's layer is an acellular layer containing randomly oriented collagen fibers. Posterior to Bowman's layer is the corneal stroma. Below the stromal layer is the membrane of Descemet. The posterior surface of the cornea is defined by the corneal endothelium, which is formed from a single layer of cells. The endothelial layer of cells covers the membrane of Descemet.

The corneal stroma is formed from about 60 connective tissue layers or "lamellae" of crisscrossing collagen fibers. The lamellae are stacked over one another and substantially parallel to the corneal surfaces. In the average human eye the cornea is a part-spherical body about 0.5 mm thick over most of its extent; the stroma itself comprises about 90% of the total corneal thickness.

Known refractive surgical techniques often involve accessing the interior corneal tissue layers. For example, laser keratectomy (photo-ablative reprofiling of the cornea) is often performed by removing the central epithelium to expose the underlying tissue to a laser. Similarly, laser assisted in situ keratomileusis (LASIK) involves folding an excised flap of corneal epithelium and stroma laterally to gain access to the central stroma for laser sculpting. Accessing this internal tissue often involves forming precise cuts through the epithelium and into the stroma, often with specialized refractive surgical cutting devices called microkeratomes and trephines. Unfortunately, these known devices suffer from significant drawbacks. U.S. Pat. Nos. 4,180,075; 4,662,370; 5,133,726; 5,215,104; 5,290,301; 5,586,980; 5,624,456; 5,643,299; 5,653,723 and 5,690,657 relate to methods and apparatus for cutting ocular tissue and are herein incorporated by reference in their entirety.

Known trephines for ocular surgery are generally designed to cut the cornea across the corneal lamella. This transverse cutting has undesirable limitations. For one, it makes the depth of the incision difficult to control. For example, the sharpness of the surgical blade cutting the cornea can effect the cut depth. Also, because the cornea flexes during cutting, the depth of the incision may depend upon both the pressure and rate of cutting. Further, the orientation of the cutting across the lamella makes it difficult to separate the cornea along a lamella at the deepest portion of the incision.

Known micro-keratomes often make use of a vacuum ring and an applanation shoe within the vacuum ring. A knife blade makes a single guillotine like cut across the front of the cornea. The depth of the cut is determined by the height of the blade below the applanation shoe. In some procedures the cut-away portion is entirely detached from the remainder of the cornea. Generally, the cut is stopped such that the cut corneal tissue is not completely detached from the remaining cornea, but instead remains connected and forms a flap. This attachment allows the flap to be folded to one side, exposing the underlying stromal tissue for laser removal. The exposed stroma is sculpted with a laser. The flap is then folded back into its original position.

Recently, it has been proposed to use a high-speed water jet instead of a blade for lamellar keratotomy, in a technique termed hydro refractive keratoplasty (HRK).

Furthermore, while the depth of the guillotine like microkeratome blade may be controlled by applanating and cutting large areas of the cornea, this applanation may raise the intra-ocular pressure, thereby damaging the eye. Mechanical cutting across the front of the cornea may also prematurely fold the flap and produce irregular astigmatism. In surgical procedures to modify the shape of the eye, mechanical cutting of the central portion of the cornea may even produce an irregular surface. This irregular surface may form a scar and reduce visual acuity.

SUMMARY OF THE INVENTION

The present invention provides systems, methods and apparatus for precisely and controllably removing an anterior portion of an eye. In particular, the techniques of the present invention permit reversible removal of the front surface of a cornea along a lamella of the corneal stroma to permit refractive surgery. The present invention is particularly useful with refractive surgical procedures such as photorefractive keratectomy (PRK), laser in situ keratomileusis (LASIK), or the like.

The methods and apparatus of the current invention permit less traumatic removal of a corneal flap for refractive surgery. The invention applanates a reduced area of the cornea by reshaping a border of a desired flap. For example, the applanation may occur along at least a portion of an annulus around a disc shaped area of the cornea. This applanation of a flap border (rather than the entire flap area) is less traumatic and reduces the resulting elevation in intra-ocular pressure.

Applanating an annular portion of the cornea flattens the corneal lamellae below the applanating surface. The flattened lamellae may then be cut with a blade, which is substantially parallel to the applanating surface. Because the lamellae are substantially parallel to the applanating surface, the blade is also substantially parallel to the lamellae. This parallel cutting helps to separate the cornea along a lamella at the depth of the incision. Since the blade is substantially parallel to the lamella, fluctuations in the distance the blade is inserted along the lamella produces little variation in the depth of the incision below the applanated surface. By controlling the separation between the blade and the applanating surface, the depth at which the lamellae separate may be precisely controlled. Therefore, by cutting the cornea with a blade that is parallel to a lamella at the maximum depth of the incision, the cornea may be cut very precisely to a predetermined depth and along a lamella.

The invention also provides for further separating the central cornea along a lamella without mechanically cutting the cornea with a sharp object such as a surgical blade. Because a border of the cornea has been cut along a lamella, the cornea may be further separated along the same lamella. For example, the operator may manually tease the lamellae apart, using gentle mechanical pulling to separate the flap from the underlying corneal tissues. Alternatively, a fluid may be injected along the lamella. If the fluid is injected as a jet, a lower pressure jet may be used for separating the stroma along a lamella than would be required for transverse cutting of the lamella. This method of separating is less likely to induce scarring.

From an apparatus aspect, the invention comprises a corneal trephine with a body having a reference surface for contacting and reshaping a border around an area of a cornea. The trephine further comprises a blade for cutting the reshaped cornea. The blade is rotatable around the body in alignment with and at a desired cut depth from the reference surface.

In one embodiment, the trephine further comprises a depth stop coupled to the body. The blade extends radially inward, and the depth stop limits the depth that the blade cuts into the cornea. This control of the cut depth into the cornea ensures that the deepest portion of the cut is under the reference surface.

In another embodiment, the trephine further comprises at least one tractional element. The tractional element releasably fixes the cornea to the reference surface. A tractional element will help maintain alignment of the reference surface with the cornea during cutting.

In a specific embodiment, the tractional elements comprise a plurality of vacuum holes. Vacuum holes are desirable tractional elements because they can releasably fix the cornea without disrupting the underlying surface. Also, the vacuum may be varied to control the fixation.

In another specific embodiment, the tractional elements comprise teeth. Teeth are desirable tractional elements because they can provide very strong fixation of the cornea, and are simple to construct.

In an additional embodiment, the trephine further comprises a rotational stop for limiting the rotation of the blade to a predetermined arc. This rotational stop provides precise control of the size of the region where the flap remains attached to the underlying tissue.

In an exemplary embodiment, the trephine comprises a ring having a flat annular surface for contacting and flattening an annular portion of a cornea. A blade for cutting the applanated cornea is supported relative to the ring and extends radially inward. The blade is rotatable along a plane substantially parallel to the surface so as to produce a cut which is substantially parallel to the flattened surface. A depth stop is coupled to the ring for controlling the depth the blade cuts into the cornea, and a rotational stop is coupled to the ring for stopping the rotation of the blade.

From a method standpoint, the invention comprises the steps of applanating a border around an area on a surface of a cornea, cutting the applanated cornea by inserting a blade into the cornea to a desired depth, guiding the inserted blade around the applanated cornea, and separating a flap of corneal tissue from a remaining corneal tissue at the cut depth.

The step of guiding may further include a step of stopping at a predetermined rotational position. This stopping creates an region where the flap is connected to the underlying tissue.

The step of separating may include separating the flap from the remaining tissue along a lamella without cutting a central portion of the cornea. This separating without cutting protects the central portion of the cornea from damage that can be caused by cutting.

The step of separating may further include a step of injecting a fluid between the lamella of the flap and remaining tissue. The injected fluid will facilitate separation along the lamella. Further, an injected fluid will cut the cornea more gently than a mechanical cut.

The injected fluid may comprise a jet. Forming a fluid into a jet provides additional control of the injected fluid for precise cutting. For example, the jet may be formed to a small diameter and directed along a lamella.

The injected fluid may be a gas or liquid. Gasses may be readily injected and are easy to pressurize. An injected liquid formed to a jet will maintain a narrow jet after leaving an orifice, thereby improving the precision of the cutting.

An alternate method of separating comprises teasing or gently pulling the flap from the underlying ocular tissue at the predetermined depth. This teasing is easy to perform and cost effective to implement.

By ablating an exposed surface of the separated cornea with a laser, a desired change in shape may be effected on the exposed surface. This ablating may be performed to correct vision. Also, the ablating is preferably performed with a pulsed excimer laser because of the smooth surfaces resulting from this type of laser ablation.

In light of the above, it is an object of the invention to cut a cornea by reshaping a surface comprising a border around an area of a cornea. It is a further object of the invention to cut the cornea in alignment with the reshaped surface. It is a yet further object of the invention to separate the cut cornea along a lamella.

DESCRIPTION OF THE SPECIFIC EMBODIMENTS

The trephine is used to cut and separate a cornea along a lamella to form a corneal flap that is separated from the remaining corneal tissue. The trephine may be used in conjunction with refractive surgeries such as laser assisted in situ keratomileusis, or other appropriate surgeries.

Figure 1A:
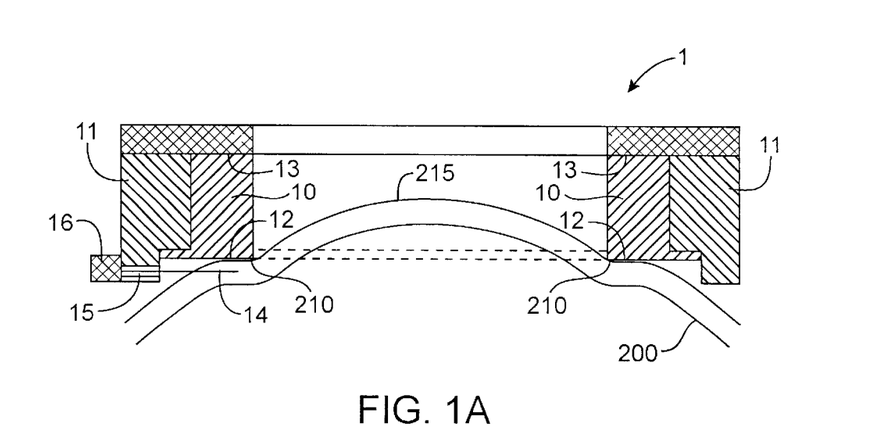
FIG. 1A is a cross sectional view of a trephine according to the principals of the present invention.
Figure 1B:
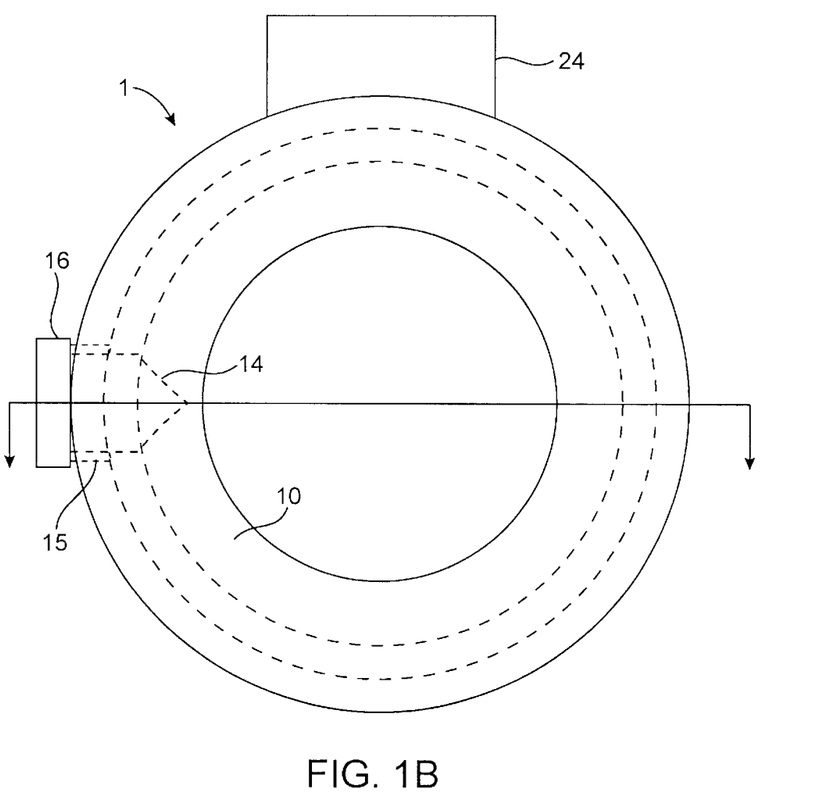
FIG. 1B is a front view of the trephine of FIG. 1A.

Turning now to the drawings, FIG. 1 illustrates a trephine 1 including a ring-shaped body 10, blade guide 11 and a cutting blade 14. Ring 10 generally has an upper surface 13 and a lower applanating surface 12. Blade guide 11 extends beyond applanating surface 12. Blade guide 11 has slot 15 for receiving blade 14. Slot 15 maintains alignment of blade 14 with applanating surface 12 and guide 11 so that blade 14 is substantially parallel to applanating surface 12. Depth stop 16 controls the depth that blade 14 is inserted into cornea 200. Rotation of blade guide 11 around ring 10 is limited by blade stop 24. Flat surface 12 applanates the surface of cornea 200 to form reshaped border 210 at least partially around area 215 of cornea 200. The area 215 of cornea 200 passes into the lumen of ring 10.

Knife blade 14 is inserted into cornea 200 below the surface of reshaped border 210. Knife blade 14 preferably has at least one sharp edge along the end of a flat surface. Alternatively, knife blade 14 may have two opposing sharp surfaces to permit bi-directional rotation while cutting cornea 200.

Guide 15 aligns knife blade 14 to be substantially parallel to reshaped border 210 on the surface of cornea 200. Knife blade 14 is rotated around area 215 of cornea 200 to cut below reshaped border 210. Blade stop 24 may be used to control the angular rotation of blade 14 around cornea 200.

Figure 2A:
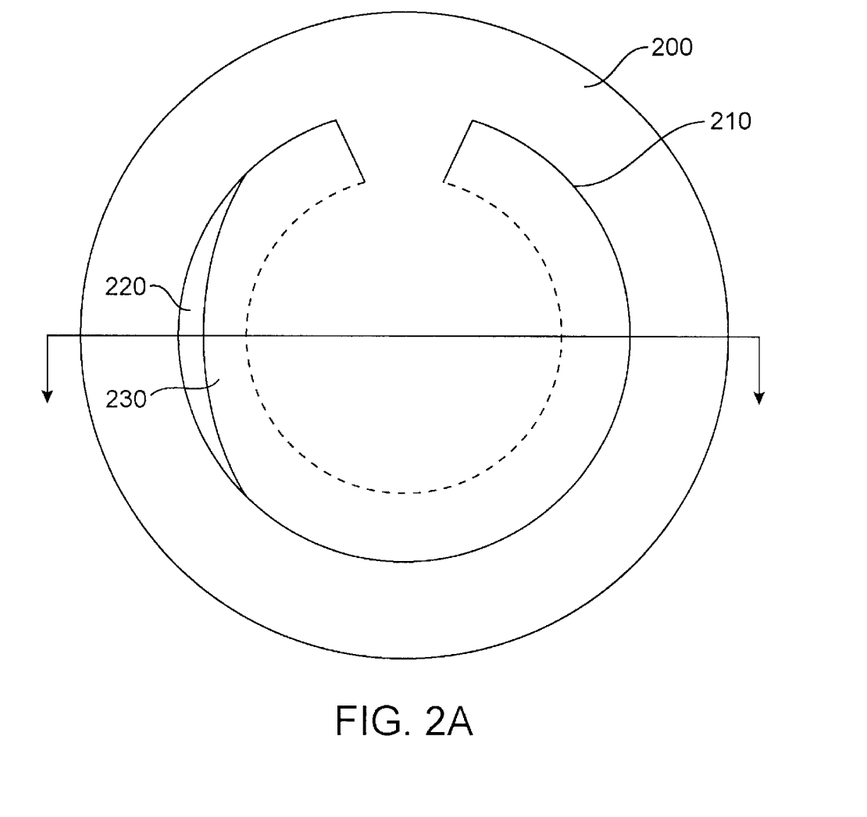
FIGS. 2A and 2B show a front view of a cut cornea and a cross section of a flap being removed along a corneal lamella.
Figure 2B:
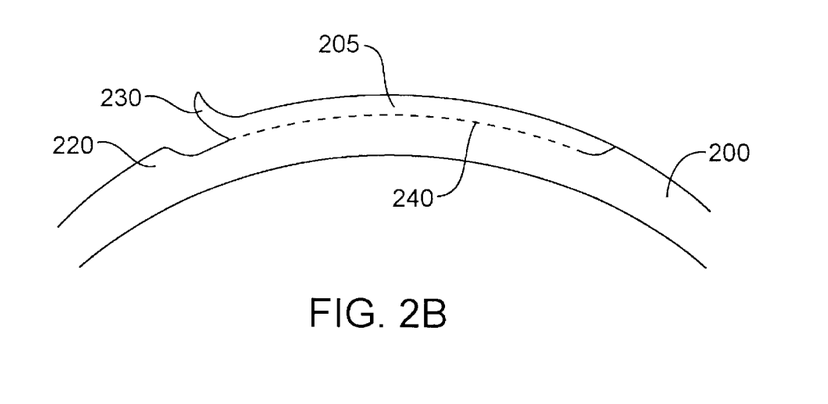

Rotation of blade 14 parallel to reshaped border 210 cuts the cornea circumferentially along lamella 240 which is below the corneal surface at a depth corresponding to the separation of blade 14 from flat surface 12. Flap 230 is separated from remaining corneal tissue 220 along lamella 240 as shown in FIG. 2.

Figure 3:
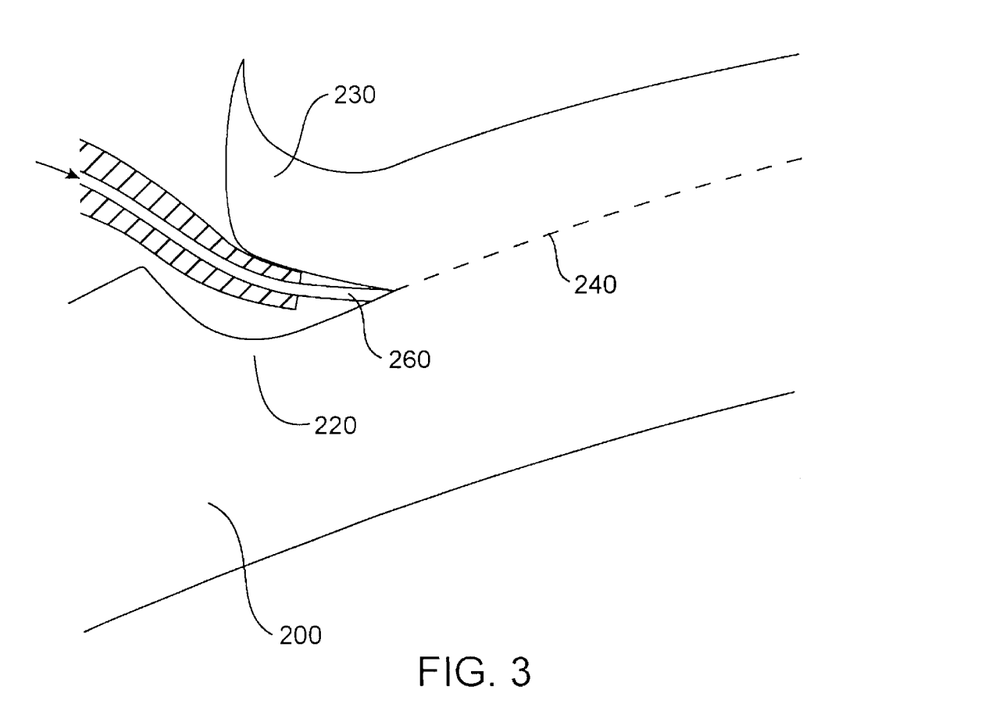
FIG. 3 is a cross sectional view of a cornea being separated along a lamella by fluid injection.

Remaining corneal tissue 220 may be further separated from flap 230 without mechanically cutting the central portion 205 of cornea 200. This separation may be accomplished by mechanically teasing or gently pulling flap 230 from remaining corneal tissue 220. In an alternate embodiment, fluid may be injected along lamella 240 to separate flap 230 from remaining corneal tissue 220 as shown in FIG. 3. The injected fluid may comprise a jet 260 as shown in FIG. 3. The injected fluid may be a liquid such as saline, or water. Alternatively, the jet may comprise a hydrated gas such as moist nitrogen, or in some embodiments, ambient air might simply be injected using a syringe.

The separation of cornea 200 into flap 230 and remaining portion 220 may be performed so that the portions remain partially attached. By controlling the width of blade stop 24, the size of the region attaching flap 230 to remaining portion 220 may be controlled. This partial separation facilitates reattaching flap 230 to remaining portion 220. The partial separation prevents the loss of flap 230 after it is removed from underlying portion 220. Also, the partial separation ensures that flap 230 and remaining portion 220 are properly aligned when flap 230 is repositioned over remaining portion 220.

Figure 4A:
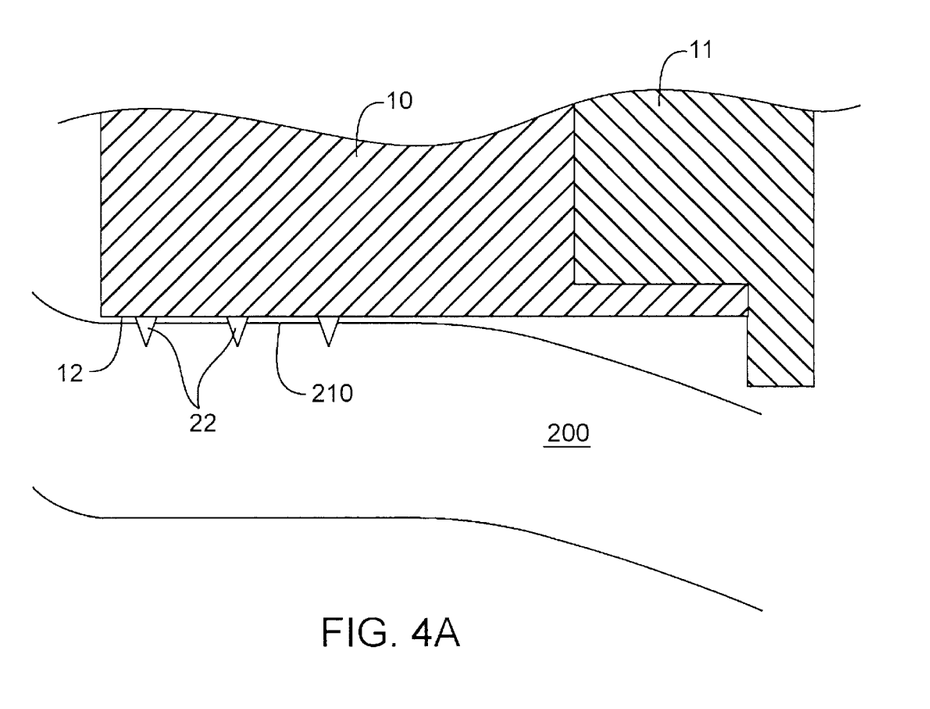
FIG. 4A is a cross sectional view of a trephine utilizing teeth as tractional elements to releasably attach the trephine to the eye.
Figure 4B:
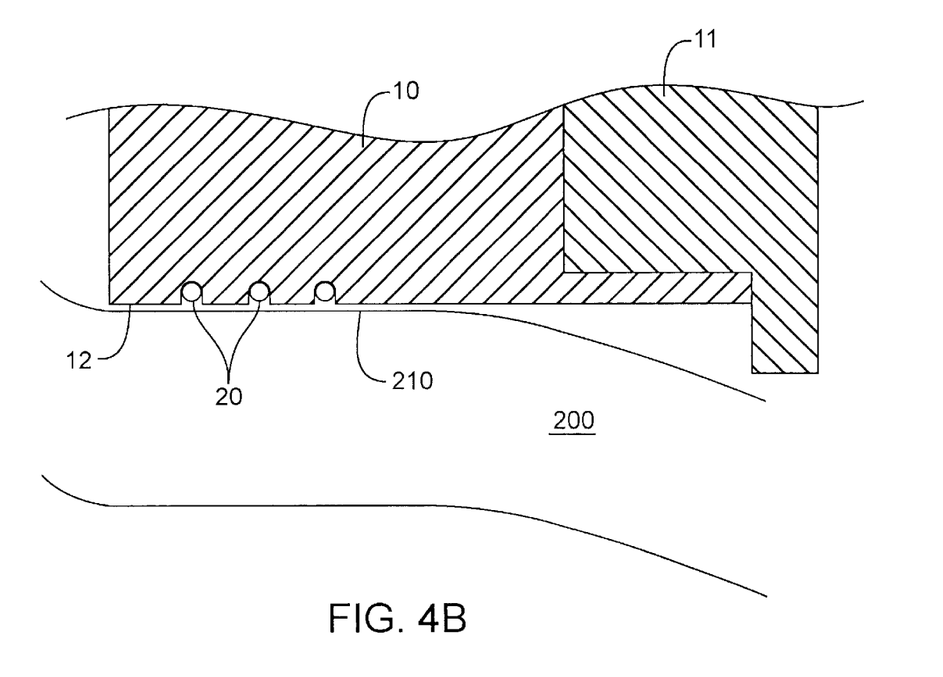
FIG. 4B shows a trephine utilizing vacuum holes as tractional elements to releasably attach the trephine to the eye.

Applanating surface 12 is preferably mechanically coupled to tractional elements such as teeth 22 of FIG. 4a, or vacuum holes 20, of FIG. 4b. These tractional elements releasably fix the eye while cornea 200 is cut with blade 14. In FIGS. 4a and 4b, tractional elements are directly coupled to flat surface 12 for releasably fixing cornea 200. However, other embodiments may be used. For example, the tractional elements may be coupled to a ring at the periphery of the cornea which releasably fixes the trephine to the conjunctiva. Although less preferred, a single vacuum hole comprising a vacuum ring substantially concentric and peripheral to applanating ring 10 of FIG. 4b may used to releasably fix the eye.

An exposed surface of the separated cornea may be treated with light to effect a change in shape. For example, an ablation may remove a layer of stroma to change its contour for various purposes, such as correcting myopia, hyperopia, and astigmatism. Such systems and methods are disclosed in the following U.S. patents and patent applications, the disclosures of which are hereby incorporated by reference in their entireties for all purposes: U.S. Pat. No. 4,665,913 issued May 19, 1987 for "Method for Ophthalmological Surgery"; U.S. Pat. No. 4,669,466 issued Jun. 2, 1987 for "Method and Apparatus for Analysis and Correction of Abnormal Refractive Errors of the Eye"; U.S. Pat. No. 4,732,148 issued Mar. 22, 1988 for "Method for Performing Ophthalmic Laser Surgery"; U.S. Pat. No. 4,770,172 issued Sep. 13, 1988 for "Method of Laser-Sculpture of the Optically Used Portion of the Cornea"; U.S. Pat. No. 4,773,414 issued Sep. 27, 1988 for "Method of Laser-Sculpture of the Optically Used Portion of the Cornea"; U.S. patent application Ser. No. 07/109,812 filed Oct. 16, 1987 for "Laser Surgery Method and Apparatus" now U.S. Pat. No. 5,108,388; U.S. Pat. No. 5,163,934 issued Nov. 17, 1992 for "Photorefractive Keratectomy"; U.S. Pat. No. 5,556,395 issued Sep. 17, 1996 for "Method and System for Laser Treatment of Refractive Error Using an Offset Image of a Rotatable Mask"; U.S. patent application Ser. No. 08/368,799, filed Jan. 4, 1995 for "Method and Apparatus for Temporal and Spatial Beam Integration" now U.S. Pat. No. 5,646,791; U.S. patent application Ser. No. 08/138,552, filed Oct. 15, 1993 for "Method and Apparatus for Combined Cylindrical and Spherical Eye Corrections"; and U.S. patent application Ser. No. 08/058,599, filed May 7, 1993 for "Method and System for Laser Treatment of Refractive Errors Using Offset Imaging" now abandoned; U.S. Pat. No. 4,840,175, issued Jun. 20, 1989 for "Methods for Modifying Corneal Curvature"; U.S. Pat. No. 4,903,695, issued Feb. 27, 1990 for "Method and Apparatus for Performing a Keratomileusis or the Like Operation".

Figure 5A:
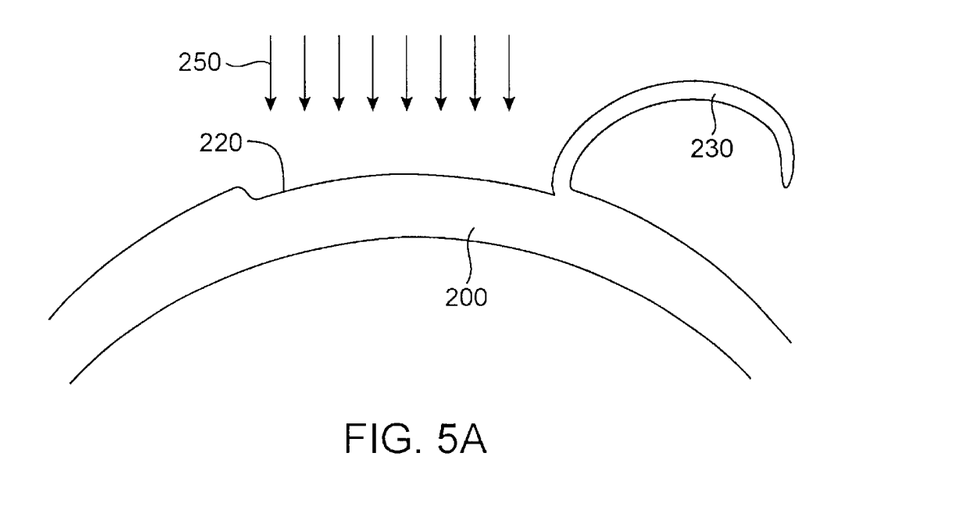
FIG. 5A is an aspect of the invention showing an exposed corneal surface being ablated with a laser after a flap has been cut away.
Figure 5B:
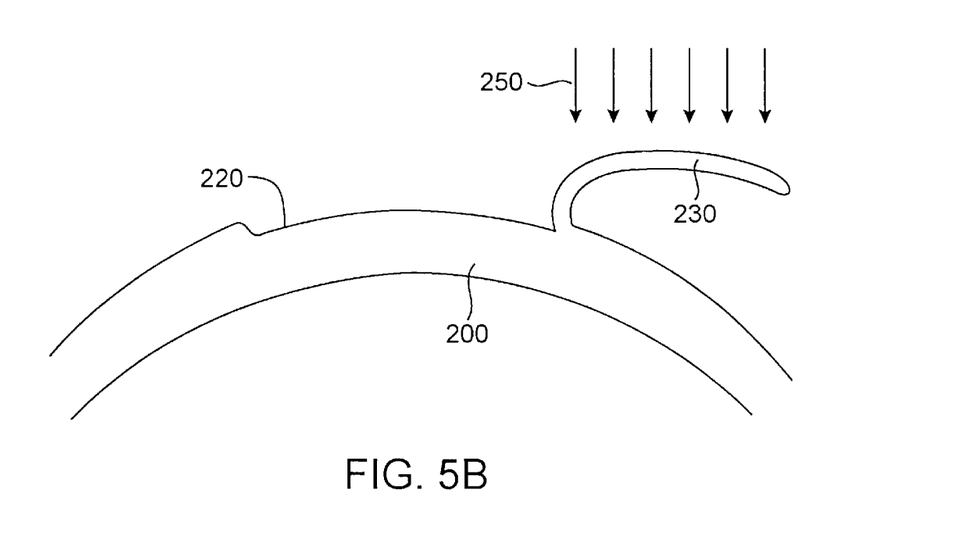
FIG. 5B is an aspect of the invention showing an exposed surface of a flap of corneal tissue being treated with a laser.

As an example, an exposed surface of remaining corneal tissue 220 may be ablated with excimer laser beam 250 to sculpt a lens on the exposed surface as shown in FIG. 5A. Flap 230 may then be reattached to remaining corneal tissue 220. Alternatively, an exposed surface of flap 230 may be ablated with excimer laser beam 250 to sculpt a lens on the exposed surface as shown in FIG. 5B. Flap 230 may then be reattached to remaining corneal tissue 220.

While the above provides a full and complete disclosure of the preferred embodiments of the invention, various modifications, alternate constructions and equivalents may be employed as desired. For example, boundaries other than circular such as elliptical or rectangular may be utilized to enclose an area of the cornea. Further lasers of other types and wavelengths, such as lasers producing electromagnetic radiation in the infrared portion of the electromagnetic spectrum, may be used to implement the invention. Therefore, the above description and illustrations should not be construed as limiting the invention, which is defined by the appended claims.

What is claimed is:

1. A corneal trephine comprising:
   a body having a reference surface for contacting and reshaping a border around an area of a cornea, the area having an axis;
   a blade for cutting the reshaped cornea, the blade being rotatable around the body in alignment with, and at a desired cut depth from, the reference surface, wherein the blade continually extends radially inward relative to the axis when the blade rotates; and, a rotational stop limiting rotation of the blade to a predetermined arc about the axis so that the cornea remains attached to the surrounding cornea.

2. The trephine of claim 1, further comprising a depth stop coupled to the body to limit the depth that the blade cuts into the cornea.

3. The trephine of claim 1, wherein the trephine comprises at least one tractional element for releasably fixing the surface to the cornea.

4. The trephine of claim 3, wherein the tractional elements comprise a plurality of vacuum holes.

5. The trephine of claim 3, wherein the tractional elements comprise teeth.

6. A trephine comprising:
    a ring having a flat annular surface for contacting and flattening an annular portion of a cornea;
    a blade for cutting the applanated cornea, the blade supported relative to the ring, the blade extending radially inward and rotatable along a plane substantially parallel to the surface so as to produce a cut which is substantially parallel to the flattened surface;
    a depth stop coupled to the ring for controlling the depth the blade cuts into the cornea; and,
    a rotational stop coupled to the ring for stopping the rotation of the blade to a predetermined arc so that the applanated cornea remains attached to the surrounding cornea.

7. A method comprising:
    applanating a border around an area on a surface of a cornea, the area having an axis;
    cutting the applanated cornea by inserting a blade into the cornea to a desired depth and guiding the inserted blade around the axis and the applanated cornea with the blade oriented radially inwardly relative to the axis;
    stopping the guiding step at a predetermined rotational position; and,
    partially separating a flap of corneal tissue from a remaining corneal tissue at the cut depth so that the flap remains attached along an uncut arc.

8. The method of claim 7, wherein the flap is separated from the remaining tissue along a lamella without cutting a central portion of the cornea.

9. A method comprising:
    applanating a border around an area on a surface of a cornea;
    cutting the applanated cornea by inserting a blade into the cornea to a desired depth and guiding the inserted blade around the applanated cornea; and,
    separating a flap of corneal tissue from a remaining corneal tissue at the cut depth, wherein the step of separating includes the step of injecting a fluid between the lamella of the flap and remaining tissue.

10. The method of claim 9, wherein the injected fluid comprises a jet.

11. The method of claim 9, wherein the injected fluid is a gas.

12. The method of claim 9, wherein the injected fluid is a liquid.

13. A method for separating a flap of a cornea from an underlying ocular tissue, the method comprising:
    reshaping a surface of the cornea by engaging the cornea with a reference surface;
    cutting around the cornea to a predetermined depth adjacent the reference surface so as to define a border of the flap;
    stopping the cutting step prior to enclosing the border; and,
    teasing the flap from the underlying ocular tissue at the predetermined depth, wherein the step of stopping is performed so that the flap remains attached to the ocular tissue.

14. A method for changing the shape of a cornea of an eye, the method comprising:
    applanating a border around an area of a surface of the cornea;
    cutting the applanated cornea by guiding a blade around the border of the cornea at a desired depth to produce a cut which is substantially parallel to the surface;
    separating a flap of the cornea disposed within the cut from a remaining tissue of the cornea so that the flap has the desired depth; and,
    ablating an exposed surface of the cornea with a laser to produce a desired change in shape.

15. The method of claim 14 wherein the step of cutting includes a first step of stopping at a predetermined depth.

16. The method of claim 15, wherein the step of guiding includes a second step of stopping at a predetermined rotational position.

17. The method of claim 14, wherein the step of cutting separates the flap from the remaining tissue along a lamella.

18. The method of claim 14, wherein the flap is separated from the remaining tissue along a lamella without cutting a central portion of the cornea.

19. The method of claim 18, wherein the step of separating includes the step of injecting a fluid between the lamella.

20. The method of claim 19, wherein the injected fluid comprises a jet.

21. The method of claim 19, wherein the injected fluid is a gas.

22. The method of claim 19, wherein the injected fluid is a liquid.

23. The method of claim 14, further comprising attaching the flap to the remaining tissue to cover the ablated surface.

24. The method of claim 14, wherein the exposed surface is ablated with a pulsed laser.

25. The method of claim 24, wherein the pulsed laser is an excimer laser.

26. A corneal trephine for use with a laser, the laser capable of ablating an exposed surface of a cornea to produce a desired change in shape, the trephine comprising:
    a ring having an annular surface for reshaping an annular area of a cornea, the area having an axis;
    a blade for cutting the applanated cornea, the blade supported relative to the ring, the blade being rotatable about the axis with the blade extending radially inward relative to the axis;
    a rotational stop coupled to the ring for stopping the rotation of the blade at a predetermined arc so that an arc along the ring remains uncut and the area of the cornea remains attached to the surrounding cornea along the uncut arc.

27. A corneal trephine comprising:
    a body having a reference surface for contacting a reshaping a border around an area of a cornea, the area having an axis;
    a blade coupled to the body for cutting the reshaped cornea, the blade being rotatable around the body in alignment with, and at a desired cut depth from, the reference surface, wherein the blade continually extends radially inward relative to the axis when the blade rotates; and, a rotational stop coupled to the body for limiting rotation of the blade to a predetermined arc about the axis so that the cornea remains attached to the surrounding cornea.

28. A trephine comprising:

a ring having a flat annular surface for contacting and flattening an annular portion of a cornea;

a blade coupled to the ring for cutting the applanated cornea, the blade extending radially inward and rotatable along a plane substantially parallel to the flattened surface so as to produce a cut which is substantially parallel to the flattened surface;

a depth stop coupled to the ring for controlling the depth the blade cuts into the cornea; and, a rotational stop coupled to the ring for stopping the rotation of the blade to a predetermined arc so that the applanated cornea remains attached to the surrounding cornea.

29. A method for changing the shape of a cornea of an eye, the method comprising:

applanating a border around an area of a surface of the cornea;

cutting the applanated cornea by guiding a blade around the cornea at a desired depth to produce a cut which is substantially parallel to the surface;

separating a flap of the cornea disposed within the cut from a remaining tissue of the cornea so that the flap has the desired depth, wherein the flap is separated from the remaining tissue along a lamella without cutting a central portion of the cornea; and, ablating an exposed surface of the cornea with a laser to produce a desired change in shape.

30. The method of claim 28, wherein the step of separating includes the step of injecting a fluid between the lamella.

31. The method of claim 30, wherein the injected fluid comprises a jet.

32. The method of claim 30, wherein the injected fluid is a gas.

33. The method of claim 30, wherein the injected fluid is a liquid.

* * * * *